United States Patent [19]
Helmuth et al.

[11] 3,954,931
[45] May 4, 1976

[54] PROCESS FOR MAKING A MOLDED VALVE HOUSING FOR A PROSTHETIC LIMB

[75] Inventors: Gene R. Helmuth, Castro Valley; Harry N. Hughes, Pleasanton, both of Calif.

[73] Assignee: The United States of America as represented by the Secretary of the Navy, Washington, D.C.

[22] Filed: Apr. 12, 1974

[21] Appl. No.: 460,323

[52] U.S. Cl. .............................. 264/90; 264/138; 264/240; 264/257; 264/313; 264/316; 264/331; 264/334
[51] Int. Cl.² .................. B29D 3/02; B29D 23/00; B29G 7/00
[58] Field of Search .......................... 264/88–90, 264/219, 222, 313, 262, DIG. 78, 257, 101, 240, 316, 334, 214, 331, 138

[56] References Cited
UNITED STATES PATENTS

| | | | |
|---|---|---|---|
| 2,429,122 | 10/1947 | Crowley | 264/90 |
| 2,962,767 | 12/1960 | Trojanowski et al. | 264/313 |
| 3,087,201 | 4/1963 | Williams et al. | 264/257 |
| 3,390,214 | 6/1968 | Woods | 264/90 |
| 3,468,991 | 9/1969 | Krug | 117/5.1 |
| 3,492,392 | 1/1970 | Kasamatsu et al. | 264/313 |
| 3,681,786 | 8/1972 | Lynch | 264/22 |
| 3,782,390 | 1/1974 | Johnson | 264/222 |

OTHER PUBLICATIONS
Randolf et al., Plastics Engineering Handbook, Reinhold, (1960) pp. 465 & 466.

*Primary Examiner*—Willard E. Hoag
*Attorney, Agent, or Firm*—R. S. Sciascia; Charles D. B. Curry

[57] ABSTRACT

A process for making a valve housing for a prosthetic socket. The process eliminates the need for a male and female mold by applying an elastic resilient separator material over the entire surface area of a housing mold, sealing one end of the material to enclose the surface area of the housing mold, applying a vacuum to the sealed material so that the material closely conforms to the entire surface area, applying an outer elastic resilient separator material to the housing mold over the reinforcing materials so as to trap the reinforcing materials to control thickness and shape, applying a vacuum thereto to force the outer elastic resilient separator and underlying reinforcement material to closely conform to the housing mold; and adding the resin molding material to impregnate the reinforcing materials.

3 Claims, 11 Drawing Figures

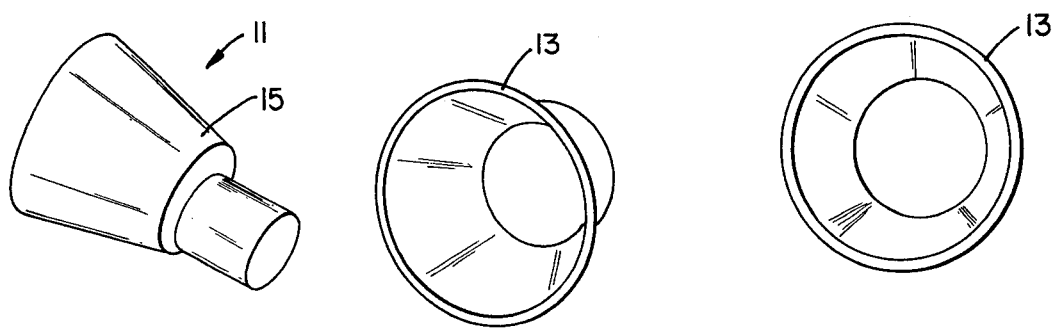
FIG_1 (PRIOR ART)
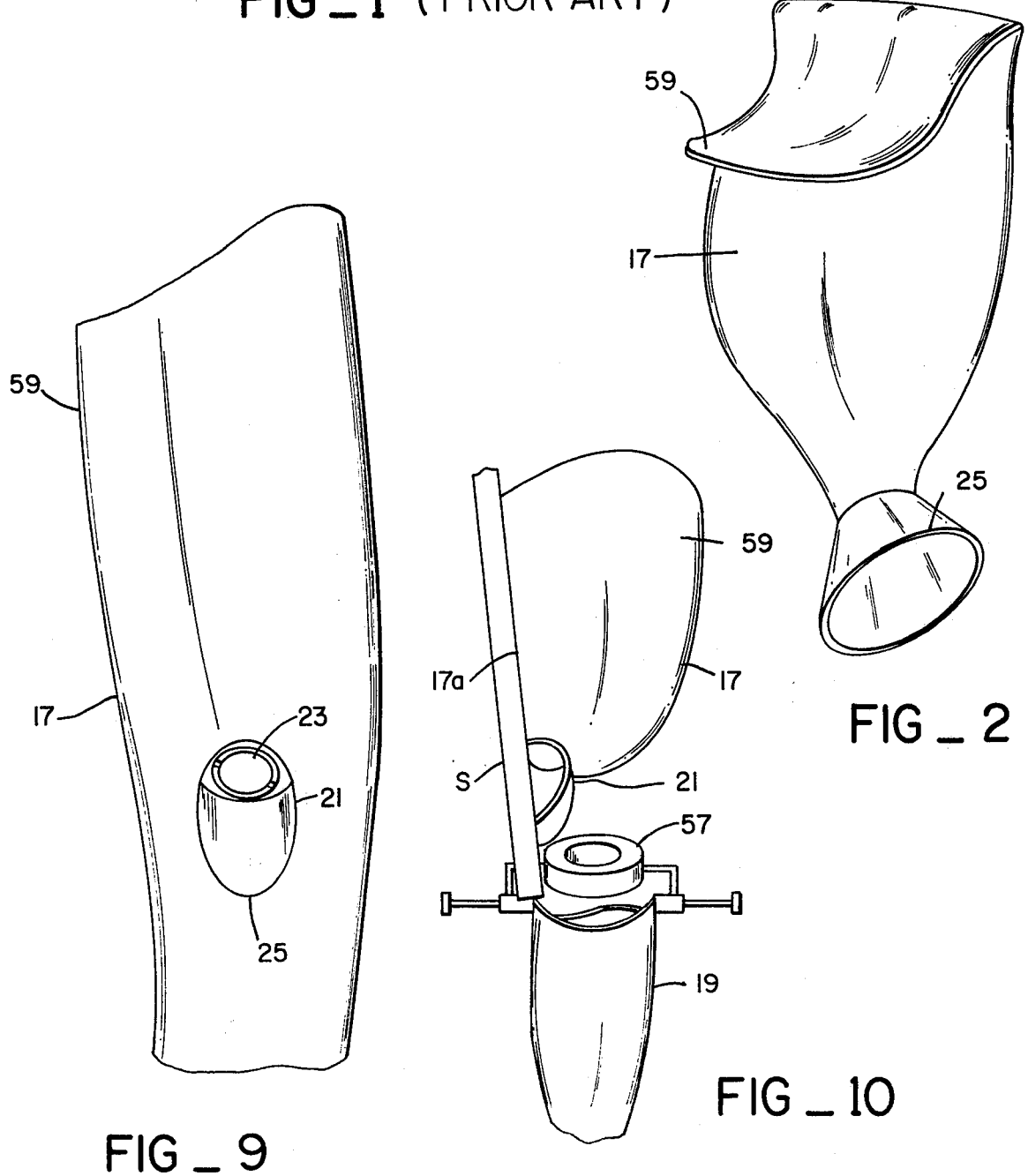
FIG_2
FIG_9
FIG_10

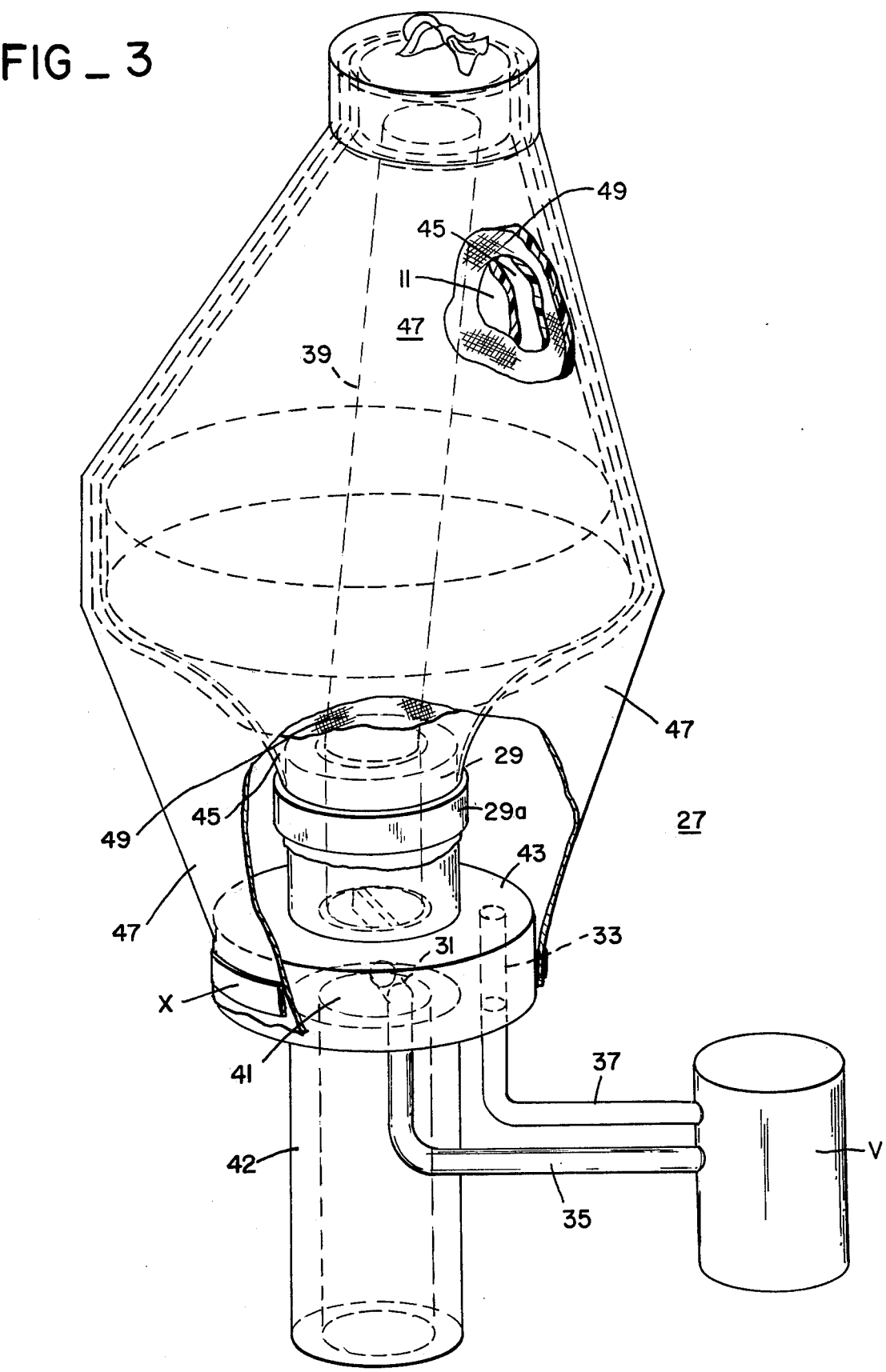
FIG_3

FIG_4

STEP I: MOUNT MOLD ON LAMINATING STAND

APPLY ELASTIC RESILIENT SEPERATOR SHEET OVER MOLD SURFACE, TIE OFF AND SEAL GAS TIGHT WITH TAPE AND APPLY VACUUM TO MAKE SHEET CONFORM TO MOLD SURFACE.

STEP II: APPLY REINFORCING MATERIAL OVER COVERED MOLD.

STEP III: APPLY EXTERNAL ELASTIC RESILIENT SEPERATOR SHEET OVER REINFORCING MATERIAL AND TIE OFF AND SEAL GAS TIGHT TO THE MOLD LAMINATING APPARATUS WITH STRING OR TAPE OR RUBBER TUBING.

STEP IV: ADD THE RESIN MOLDING MATERIAL AND APPLY VACUUM TO FORCE THE OUTER ELASTIC RESILIENT SHEET INTO CONFORMATION OF MOLD SHAPE.

STEP IV A: REMOVE FROM MOLD AND TRIM.

STEP V: FIT AND ATTACH HOUSING AS IN FIG_2 TO SOCKET AND FINISH SOCKET.

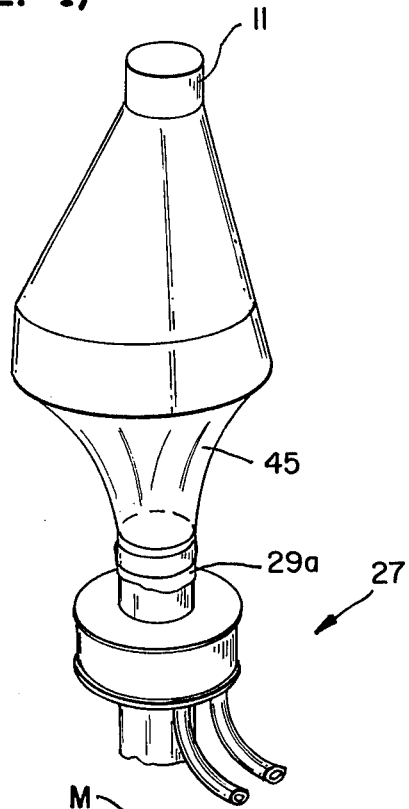
FIG_5 (STEP I)
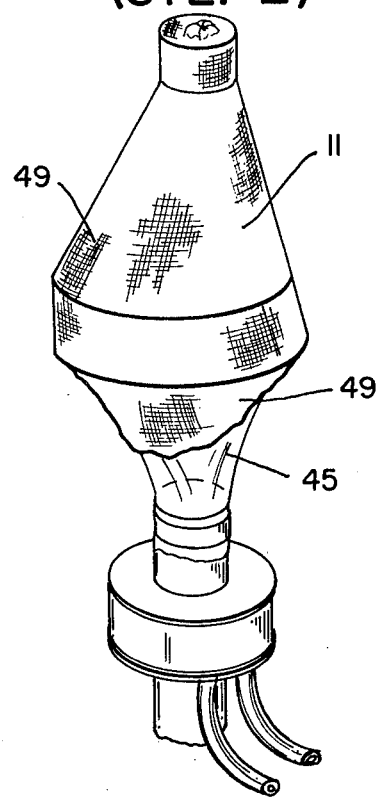
FIG_6 (STEP II)
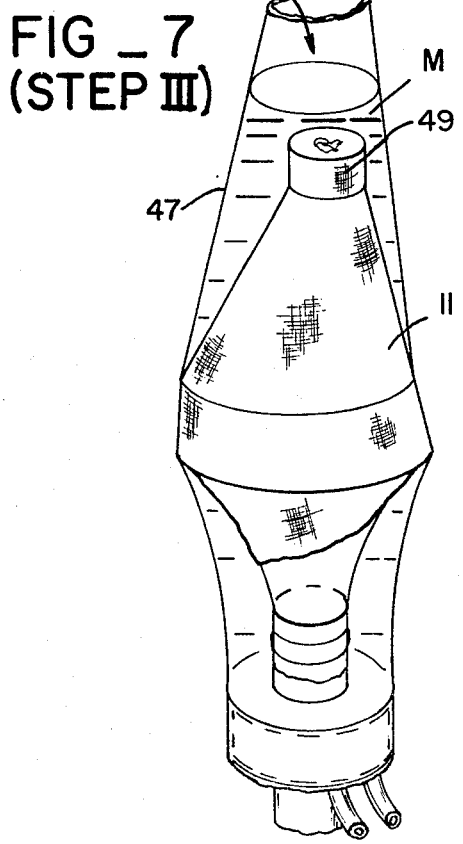
FIG_7 (STEP III)
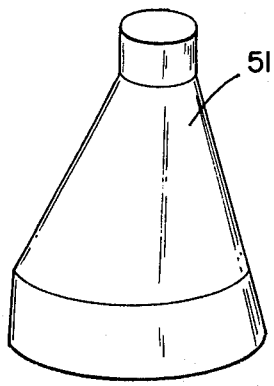
FIG_8A (STEP IV A)
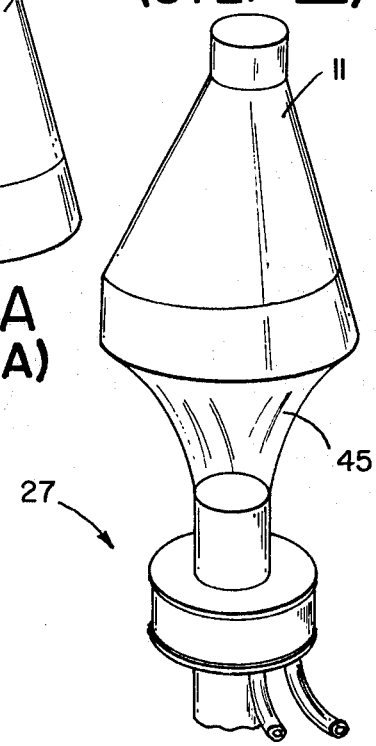
FIG_8 (STEP IV)

3,954,931

PROCESS FOR MAKING A MOLDED VALVE HOUSING FOR A PROSTHETIC LIMB

BACKGROUND OF THE INVENTION

1. Field of the Invention

The subject matter of the present invention relates to a molding process and more particularly to a process for making a molded valve housing for a prosthetic socket.

2. Description of the Prior Art

The prior method for making a molded housing for a prosthetic socket required the use of a male and female mold. This method did not provide a proper color or texture since the same material which was used for the socket could not be used in the conventional male/female mold process.

SUMMARY OF THE INVENTION

Briefly, the present invention is a process for making a valve housing for a prosthetic socket. The process eliminates the need for a male and female mold by applying an elastic resilient separator material over the entire surface area of a housing mold, sealing one end of the material to enclose the surface area of the housing mold, applying a vacuum to the sealed material so that the material closely conforms to the entire surface area, applying an outer elastic resilient separator material to the housing mold over the reinforcing materials so as to trap the reinforcing materials to control thickness and shape, applying a vacuum thereto to force the outer elastic resilient separator and underlying reinforcement material to closely conform to the housing mold; and adding the resin molding material to impregnate the reinforcing materials.

This allows the housing to be made of the same material used in the final lamination when finishing the prosthesis. By using the same material and same color texture the valve housing blends in with the prosthesis and presents a more esthetic finish.

STATEMENT OF THE OBJECTS OF THE INVENTION

A primary object of the present invention is to provide a process which will eliminate the use of the male/female mold combination when making a finished molded valve housing for a prosthesis.

Another object of the present invention is to provide a process which allows the use of the same material used in the making of the prosthesis.

Another object of the present invention is to provide a molded valve housing which blends with the prosthetic socket and provides an esthetic finish.

Other objects, advantages and novel features of the invention will become apparent from the following detailed description of the invention when considered in conjunction with the accompanying drawings wherein:

BRIEF DESCRIPTION OF THE DRAWINGS

FIG. 1 depicts the valve housing molds used in the prior process.

FIG. 2 is an isometric view of an unfinished prosthetic socket including the valve and the valve housing before the esthetic finish is applied.

FIG. 3 is an isometric view of the vacuum operated mold laminating apparatus and including the mold and mold mount.

FIG. 4 is a flow diagram illustrating the improved valve housing molding process in combination with the process for installation of the valve housing.

FIG. 5 (Step I of FIG. 4) depicts the mold mounted on the laminating apparatus illustrated in FIG. 3 and specifically illustrating the process step of applying the elastic resilient separator material over the entire exterior functional surface area of the mold.

FIG. 6 (Step II of FIG. 4) depicts the mold mounted on the laminating apparatus illustrated in FIG. 3 and specifically illustrating the process step of applying a fiber stockinette reinforcement over the elastic resilient separator material and the mold.

FIG. 7 (Step III of FIG. 4) depicts the mold mounted on the laminating apparatus illustrated in FIG. 3 and specifically illustrating the process step of applying the outer elastic resilient separator over the stockinette and illustrating the process step of introducing the liquid molding material into the bag.

FIG. 8 (Step IV of FIG. 4) depicts the mold mounted on the laminating apparatus illustrated in FIG. 3 and specifically shows the molded section after polymerization.

FIG. 8A (Step IVA of FIG. 4) is the finished molded valve housing after being removed from the laminating apparatus illustrated in FIG. 8.

FIg. 9 is an isometric view of the finished prosthetic socket with the valve housing in place.

FIG. 10 (Step V of FIG. 4) is an isometric view of an unfinished socket and shin and including the valve and the valve housing, illustrating the method for aligning the housing with the exterior wall of the socket.

DESCRIPTION OF THE PREFERRED EMBODIMENT

Referring to FIG. 1 (prior art) the valve housing mold 11 is comprised of female mold 13 and male mold 15. The molding material M is poured and set in the conventional manner which is well known in the art. A complete description of the prior art process for molding a valve housing for a suction socket is described in *Orthotics and Prosthetics*, September 1972 in an article entitled "Valve Housing for Use in Forming and Finishing Above-Knee Suction Sockets" by Harry N. Hughes and Gene Helmuth.

Referring to FIGS. 2, 9 and 10 a prosthetic limb is generally comprised of prosthetic socket 17, shin and foot 19, and valve area 21. The valve area 21 is comprised of valve 23 and its accompanying housing 25. When a prosthetic socket is being finished much of the time devoted to achieving a finished socket is directed towards providing a neat esthetic appearance especially in the valve area 21. However, when the above described conventional methods are used to mold the valve housing, the material used for finishing the prostheis limb cannot be used since the finishing material cannot be molded into the conventional female/male mold. The ultimate result is a poor cosmetic finish since the valve housing 25 will not blend with the exterior finish of the prosthetic limb. If the valve housing 25 is made of the same material used in the final limb lamination the valve housing will blend with the socket to provide an acceptable esthetic finish.

The improved process for molding the valve housing combination with the process for making the valve housing for a prosthetic limb is considered the nexus of the present invention.

The improved process is described herein below. The apparatus for making the valve housing 25 illustrated in FIGS. 2, 3, (Steps I–V of FIG. 4) and 10 is illustrated in FIG. 3 and comprised of a laminating stand 27, mounting hole 29, and vacuum passages 31 and 33. Vacuum passages 31 and 33 are coupled to the vacuum source V via vacuum lines 35 and 37 respectively. Mold 11 which may be made of plaster or the like is mounted on one end of vertical support leg 39. Vertical support leg 39 extends into the opening mounting hole 29. Vertical support leg 39 is aligned to contiguously mate with the interior walls of mounting hole 29 while allowing for the air to be withdrawn through the space created therebetween by the low pressure (vacuum) source V. Laminating stand 27 further includes internal vacuum ring 41 and external vacuum ring 43. Vacuum passage 31 is operatively coupled to ring 41 while vacuum passage 33 is formed as an integral part by a vertical wall of external vacuum ring 43.

Vacuum passage 31 provides the proper vacuum seal for the internal flexible sheet 45 which surrounds mold 11. When the vacuum is applied from the vacuum source V through line 35 the flexible sheet 45 will contract to come in contact with the surface area of mold 11. When the vacuum is applied from the vacuum source V through vacuum line 37 the external flexible sheet 47 contracts around the exterior surface of ring base 42. This leaves the upper portion P open for the purpose of inserting the liquid molding material M. However, it is not necessary to apply vacuum before introducing the liquid resin into the outer elastic resilient separator.

The procedures for making the valve housing are as follows: Referring to FIGS. 3 and 5 in conjunction with FIG. 4 (Step I), mold 11 is mounted on laminating stand 27 as described above. Elastic resilient separator material 45 is applied over the entire functional surface area of mold 11 to serve as separator between mold 11 and molding material M. Material 45 is preferably a film of polyvinyl-alcohol or its equivalent. Material 45 is secured to mounting body 29a by a tie of string or tape or an adhesive material or their equivalents. A vacuum from vacuum source V is applied to ring 41, vacuum passage 31 via line 35. The vacuum is applied until the material 45 substantially covers the entire functional surface area of mold 11.

Referring to FIGS. 3 and 6 in conjunction with FIG. 4 (Step II), a fiber reinforcement material 49 in the form of a stockinette is applied over the covered mold 11. Reinforcement material 49 is secured at point X.

Referring to FIGS. 3 and 6 in conjunction with FIG. 4 (Step III) the external flexible sheet 47 is applied over reinforcement material 49. Material 47 is also preferably a polyvinyl-alcohol film. The lower portion of sheet 47 is secured around external vacuum ring 43 at point X by a tie of string or tape or an adhesive material or its equivalent forming a mold cavity between the external flexible sheet 47 and the elastic separator material 45 covering the mold element 11. The fabric reinforcement material 49 is held in place by the vacuum applied through vacuum passage 33 from the vacuum source V via line 37.

Referring to FIGS. 3, 7 and 8 in conjunction with FIG. 4 (Steps IV and IVA) molding material M is introduced into the opening in the upper portion of sheet 47. The opening in the upper portion of sheet 47 is then secured gas tight and the vacuum pressure is increased in line 37 to constrict sheet 47 into the shape of mold 11 at a slightly larger diameter than mold 11.

The molding material is preferably a liquid resin, that has been catalyzed and will readily polymerize.

Referring to FIGS. 8 and 8A in conjunction with FIG. 4 (Steps IV and IVA) the mold material M or resin has polymerized and is rigid the sheet 47 is removed and the excess molding material M is trimmed from finished housing 51. After additional trimming, housing is ready for installation. The installation of finished housing 51 is described below.

Referring to FIGS. 2, 4, 9 and 10 (part of Step V of FIG. 4), after socket 17 is laminated some of the laminate is removed around the face of valve 23 to allow placement of finished housing 51 which is designed to fit snugly over valve 23. Finished housing 51 is then shaped to the desired contour preferably by aligning with a scale S so that housing 51 is generally flush with the exterior wall 17a of socket 17 as illustrated in FIG. 10.

Referring to FIGS. 4 (Step V) and 10, after shaping, housing 51 is filled with Plaster-of-Paris or clay and a plastic like foam is introduced below the socket 17 and the knee 57. After the foaming operation the thigh section 59 is given its final shape and an outer laminate which is the same material as stockinette 49 is applied to the socket 17 surface. The foaming and shaping operation are well known procedures in the art. When the lamination has cured, socket 17 is trimmed and the Plaster-of-Paris filler removed, and the thigh section is attached to the shin and foot 19. The finished socket is illustrated in FIG. 9.

Since the valve housing 51 is made of the same material, the housing will have the same color and texture of the prosthesis and will blend with the prosthesis.

What is claimed is:
1. A process for making a molded object comprising the steps of:
  a. applying a first layer of elastic resilient separator material over a molding surface of a mold;
  b. sealing the perimeter of said first layer of elastic material to enclose said molding surface of said mold;
  c. applying a first vacuum to the volume contained by said sealed first layer of elastic material so that said first layer of elastic material conformally encompasses said molding surface of said mold to essentially seal off said mold from the atmosphere;
  d. applying resilient fiber reinforcement material over said first layer of elastic material;
  e. applying a second layer of elastic resilient material having a tubular shape and a first end and a second end over and around said reinforcing material;
  f. sealing said first end of said second layer of elastic material in such a way as to form a mold cavity between said layers of elastic material;
  g. introducing a hardenable molding material into an unsealed second end of said second layer of elastic material;
  h. sealing said unsealed second end of said second layer of elastic material;
  i. applying a second vacuum to the volume contained in-between said second layer of elastic material and said first layer of elastic material while simultaneously applying said first vacuum;
  j. permitting said hardenable molding material to harden; and k. removing said hardened molding material with said reinforcing material imbedded therein from said mold and removing said first layer of elastic material from the inner surface and said second layer of elastic material from the outer surface of said hardened molding material with said reinforcing material imbedded therein to produce said molded object.

2. The process of claim 1 wherein said molded object is a valve housing for a suction suspension valve of a prosthesis and is composed of the same material as said prosthesis.

3. The process of claim 1 wherein said molding material is a polymerizable material further including the steps of introducing a polymerizing agent while applying said vacuum.

* * * * *